(12) United States Patent
Myrick et al.

(10) Patent No.: US 8,213,012 B2
(45) Date of Patent: Jul. 3, 2012

(54) STABILITY FOR OPTICAL COMPUTING SYSTEM

(75) Inventors: Michael L. Myrick, Irmo, SC (US);
Robert P. Freese, Pittsboro, NC (US);
William Soltmann, Columbia, SC (US);
David L. Perkins, Irmo, SC (US);
Leonard Zheleznyak, Pittsford, NY (US)

(73) Assignee: Halliburton Energy Services, Inc., Houston, TX (US)

( * ) Notice: Subject to any disclaimer, the term of this patent is extended or adjusted under 35 U.S.C. 154(b) by 37 days.

(21) Appl. No.: 12/530,271

(22) PCT Filed: Mar. 27, 2008

(86) PCT No.: PCT/US2008/058396
§ 371 (c)(1),
(2), (4) Date: Mar. 29, 2010

(87) PCT Pub. No.: WO2008/121693
PCT Pub. Date: Oct. 9, 2008

(65) Prior Publication Data
US 2010/0195105 A1 Aug. 5, 2010

Related U.S. Application Data

(60) Provisional application No. 60/920,996, filed on Mar. 30, 2007, provisional application No. 60/856,192, filed on Nov. 2, 2006.

(51) Int. Cl.
*G01N 21/00* (2006.01)

(52) U.S. Cl. .................................. 356/433; 356/432
(58) Field of Classification Search .......... 356/432–442, 356/448, 39–42, 319, 326, 300, 337–343, 356/317–318, 301; 250/252.1, 576, 574, 250/461.2, 338.5, 200, 216, 573, 336.1
See application file for complete search history.

(56) References Cited

U.S. PATENT DOCUMENTS

| | | | |
|---|---|---|---|
| 4,968,148 A * | 11/1990 | Chow et al. | 356/427 |
| 6,980,285 B1 | 12/2005 | Hansen | |
| 6,982,431 B2 | 1/2006 | Modlin et al. | |
| 2006/0051036 A1 | 3/2006 | Treado et al. | |
| 2006/0158734 A1* | 7/2006 | Schuurmans et al. | 359/485 |
| 2009/0050827 A1* | 2/2009 | Takahashi et al. | 250/577 |

OTHER PUBLICATIONS

International Search Report for PCT/US2008/058396.

* cited by examiner

*Primary Examiner* — Tri T Ton

(57) ABSTRACT

The present subject matter relates to methods of high-speed analysis of product samples. Light is directed to a portion of a product under analysis and reflected from or transmitted through the product toward an optical detector. Signals for the detector are compared with reference signals based on a portion of the illuminating light passing through a reference element to determine characteristics of the product under analysis. Temperature within the analysis system is monitored and the output signals of the optical detectors are compensated or corrections are made within the analysis calculations to compensate or correct for the system temperature. The products under analysis may be stationary, moved by an inspection point by conveyor or other means, or may be contained within a container, the container including a window portion through which the product illuminating light may pass.

18 Claims, 1 Drawing Sheet

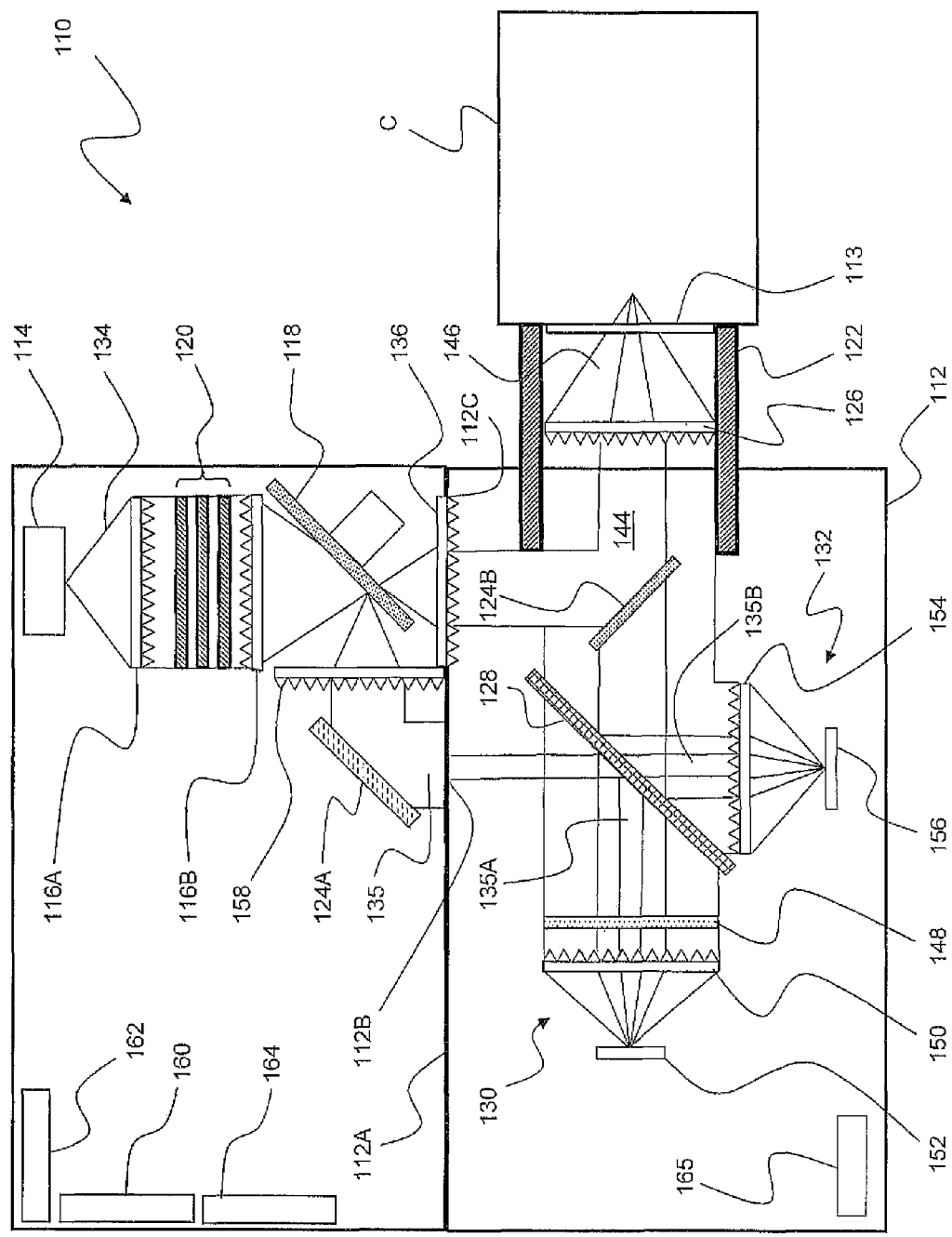

STABILITY FOR OPTICAL COMPUTING SYSTEM

CROSS-REFERENCE TO RELATED APPLICATION

The present application is related to U.S. Provisional Patent Application Ser. No. 60/856,192 filed Nov. 2, 2006, the content of which is incorporated herein by reference. The present application claims priority to U.S. Provisional Patent Application Ser. No. 60/920,996 file Mar. 30, 2007.

FIELD OF THE INVENTION

The present invention relates to improvements related to system design, fabrication and operation of multivariate optical elements. More particularly, the invention relates to methodologies of using multivariate optical computing systems to illuminate a sample in which information about the sample can be analyzed from the reflected or transmitted light in real time or near real time.

BACKGROUND OF THE INVENTION

Light conveys information through data. When light interacts with matter, for example, it carries away information about the physical and chemical properties of the matter. A property of the light, for example, its intensity, may be measured and interpreted to provide information about the matter with which it interacted. That is, the data carried by the light through its intensity may be measured to derive information about the matter. Similarly, in optical communications systems, light data is manipulated to convey information over an optical transmission medium, for example fiber optic cable. The data is measured when the light signal is received to derive information.

In general, a simple measurement of light intensity is difficult to convert to information because it likely contains interfering data. That is, several factors may contribute to the intensity of light, even in a relatively restricted wavelength range. It is often impossible to adequately measure the data relating to one of these factors since the contribution of the other factors is unknown.

It is possible, however, to derive information from light. An estimate may be obtained, for example, by separating light from several samples into wavelength bands and performing a multiple linear regression of the intensity of these bands against the results of conventional measurements of the desired information for each sample. For example, a polymer sample may be illuminated so that light from the polymer carries information such as the sample's ethylene content. Light from each of several samples may be directed to a series of bandpass filters which separate predetermined wavelength bands from the light. Light detectors following the bandpass filters measure the intensity of each light band. If the ethylene content of each polymer sample is measured using conventional means, a multiple linear regression of ten measured bandpass intensities against the measured ethylene content for each sample may produce an equation such as:

$$y = a_0 + a_1 w_1 + a_2 w_2 + \ldots + a_{10} w_{10} \quad \text{(``Equation 1'')}$$

where y is ethylene content, $a_n$ are constants determined by the regression analysis, and $w_n$ is light intensity for each wavelength band.

Equation 1 may be used to estimate ethylene content of subsequent samples of the same polymer type. Depending on the circumstances, however, the estimate may be unacceptably inaccurate since factors other than ethylene may affect the intensity of the wavelength bands. These other factors may not change from one sample to the next in a manner consistent with ethylene.

A more accurate estimate may be obtained by compressing the data carried by the light into principal components. To obtain the principal components, spectroscopic data is collected for a variety of samples of the same type of light, for example from illuminated samples of the same type of polymer. For example, the light samples may be spread into their wavelength spectra by a spectrograph so that the magnitude of each light sample at each wavelength may be measured. This data is then pooled and subjected to a linear-algebraic process known as singular value decomposition (SVD). SVD is at the heart of principal component analysis, which should be well understood in this art. Briefly, principal component analysis is a dimension reduction technique, which takes m spectra with n independent variables and constructs a new set of eigenvectors that are linear combinations of the original variables. The eigenvectors may be considered a new set of plotting axes. The primary axis, termed the first principal component, is the vector, which describes most of the data variability. Subsequent principal components describe successively less sample variability, until only noise is described by the higher order principal components.

Typically, the principal components are determined as normalized vectors. Thus, each component of a light sample may be expressed as $x_n z_n$, where $x_n$ is a scalar multiplier and $z_n$ is the normalized component vector for the $n_{th}$ component. That is, $z_n$ is a vector in a multi-dimensional space where each wavelength is a dimension. As should be well understood, normalization determines values for a component at each wavelength so that the component maintains it shape and so that the length of the principal component vector is equal to one. Thus, each normalized component vector has a shape and a magnitude so that the components may be used as the basic building blocks of all light samples having those principal components. Accordingly, each light sample may be described in the following format by the combination of the normalized principal components multiplied by the appropriate scalar multipliers:

$$x_1 z_1 + x_2 z_2 + \ldots + x_n z_n.$$

The scalar multipliers $x_n$ may be considered the "magnitudes" of the principal components in a given light sample when the principal components are understood to have a standardized magnitude as provided by normalization.

Because the principal components are orthogonal, they may be used in a relatively straightforward mathematical procedure to decompose a light sample into the component magnitudes, which accurately describe the data in the original sample. Since the original light sample may also be considered a vector in the multi-dimensional wavelength space, the dot product of the original signal vector with a principal component vector is the magnitude of the original signal in the direction of the normalized component vector. That is, it is the magnitude of the normalized principal component present in the original signal. This is analogous to breaking a vector in a three dimensional Cartesian space into its X, Y and Z components. The dot product of the three-dimensional vector with each axis vector, assuming each axis vector has a magnitude of 1, gives the magnitude of the three dimensional vector in each of the three directions. The dot product of the original signal and some other vector that is not perpendicular to the other three dimensions provides redundant data, since this magnitude is already contributed by two or more of the orthogonal axes.

Because the principal components are orthogonal, or perpendicular, to each other, the dot, or direct, product of any principal component with any other principal component is zero. Physically, this means that the components do not interfere with each other. If data is altered to change the magnitude of one component in the original light signal, the other components remain unchanged. In the analogous Cartesian example, reduction of the X component of the three dimensional vector does not affect the magnitudes of the Y and Z components.

Principal component analysis provides the fewest orthogonal components that can accurately describe the data carried by the light samples. Thus, in a mathematical sense, the principal components are components of the original light that do not interfere with each other and that represent the most compact description of the entire data carried by the light. Physically, each principal component is a light signal that forms a part of the original light signal. Each has a shape over some wavelength range within the original wavelength range. Summing the principal components produces the original signal, provided each component has the proper magnitude.

The principal components comprise a compression of the data carried by the total light signal. In a physical sense, the shape and wavelength range of the principal components describe what data is in the total light signal while the magnitude of each component describes how much of that data is there. If several light samples contain the same types of data, but in differing amounts, then a single set of principal components may be used to exactly describe (except for noise) each light sample by applying appropriate magnitudes to the components.

The principal components may be used to accurately estimate information carried by the light. For example, suppose samples of a certain brand of gasoline, when illuminated, produce light having the same principal components. Spreading each light sample with a spectrograph may produce wavelength spectra having shapes that vary from one gasoline sample to another. The differences may be due to any of several factors, for example differences in octane rating or lead content.

The differences in the sample spectra may be described as differences in the magnitudes of the principal components. For example, the gasoline samples might have four principal components. The magnitudes $x_n$ of these components in one sample might be J, K, L, and M, whereas in the next sample the magnitudes may be 0.94 J, 1.07K, 1.13 L and 0.86M. As noted above, once the principal components are determined, these magnitudes exactly describe their respective light samples.

Refineries desiring to periodically measure octane rating in their product may derive the octane information from the component magnitudes. Octane rating may be dependent upon data in more than one of the components. Octane rating may also be determined through conventional chemical analysis. Thus, if the component magnitudes and octane rating for each of several gasoline samples are measured, a multiple linear regression analysis may be performed for the component magnitudes against octane rating to provide an equation such as:

$$y=a_0+a_1x_1+a_2x_2+a_3x_3+a_4x4 \qquad \text{(``Equation 2'')}$$

where y is octane rating, $a_n$ are constants determined by the regression analysis, and $x_1$, $x_2$, $x_3$ and $x_4$ are the first, second, third and fourth principal component magnitudes, respectively.

Using Equation 2, which may be referred to as a regression vector, refineries may accurately estimate octane rating of subsequent gasoline samples. Conventional systems perform regression vector calculations by computer, based on spectrograph measurements of the light sample by wavelength. The spectrograph system spreads the light sample into its spectrum and measures the intensity of the light at each wavelength over the spectrum wavelength range. If the regression vector in the Equation 2 form is used, the computer reads the intensity data and decomposes the light sample into the principal component magnitudes $x_n$ by determining the dot product of the total signal with each component. The component magnitudes are then applied to the regression equation to determine octane rating.

To simplify the procedure, however, the regression vector is typically converted to a form that is a function of wavelength so that only one dot product is performed. Each normalized principal component vector $z_n$ has a value over all or part of the total wavelength range. If each wavelength value of each component vector is multiplied by the regression constant $a_n$ corresponding to the component vector, and if the resulting weighted principal components are summed by wavelength, the regression vector takes the following form:

$$y=a_0+b_1u_1+b_2u_2+\ldots+b_nu_n \qquad \text{(``Equation 3'')}$$

where y is octane rating, $a_0$ is the first regression constant from Equation 2, $b_n$ is the sum of the multiple of each regression constant $a_n$ from Equation 2 and the value of its respective normalized regression vector at wavelength n, and $u_n$ is the intensity of the light sample at wavelength n. Thus, the new constants define a vector in wavelength space that directly describes octane rating. The regression vector in a form as in Equation 3 represents the dot product of a light sample with this vector.

Normalization of the principal components provides the components with an arbitrary value for use during the regression analysis. Accordingly, it is very unlikely that the dot product result produced by the regression vector will be equal to the actual octane rating. The number will, however, be proportional to the octane rating. The proportionality factor may be determined by measuring octane rating of one or more samples by conventional means and comparing the result to the number produced by the regression vector. Thereafter, the computer can simply scale the dot product of the regression vector and spectrum to produce a number approximately equal to the octane rating.

In a conventional spectroscopy analysis system, a laser directs light to a sample by a bandpass filter, a beam splitter, a lens and a fiber optic cable. Light is reflected back through the cable and the beam splitter to another lens to a spectrograph. The spectrograph separates light from the illuminated sample by wavelength so that a detection device such as a charge couple detector can measure the intensity of the light at each wavelength. The charge couple detector is controlled by controller and cooled by a cooler. The detection device measures the light intensity of light from the spectrograph at each wavelength and outputs this data digitally to a computer, which stores the light intensity over the wavelength range. The computer also stores a previously derived regression vector for the desired sample property, for example octane, and sums the multiple of the light intensity and the regression vector intensity at each wavelength over the sampled wavelength range, thereby obtaining the dot product of the light from the substance and the regression vector. Since this number is proportional to octane rating, the octane rating of the sample is identified.

Since the spectrograph separates the sample light into its wavelengths, a detector is needed that can detect and distinguish the relatively small amounts of light at each wavelength. Charge couple devices provide high sensitivity throughout the visible spectral region and into the near infrared with extremely low noise. These devices also provide high quantum efficiency, long lifetime, imaging capability and solid-state characteristics. Unfortunately, however, charge couple devices and their required operational instrumentation are very expensive. Furthermore, the devices are sensitive to environmental conditions. In a refinery, for example, they must be protected from explosion, vibration and temperature fluctuations and are often placed in protective housings approximately the size of a refrigerator. The power requirements, cooling requirements, cost, complexity and maintenance requirements of these systems have made them impractical in many applications.

Multivariate optical computing (MOC) is a powerful predictive spectroscopic technique that incorporates a multiwavelength spectral weighting directly into analytical instrumentation. This is in contrast to traditional data collection routines where digitized spectral data is post processed with a computer to correlate spectral signal with analyte concentration. Previous work has focused on performing such spectral weightings by employing interference filters called Multivariate Optical Elements (MOEs). Other researchers have realized comparable results by controlling the staring or integration time for each wavelength during the data collection process. All-optical computing methods have been shown to produce similar multivariate calibration models, but the measurement precision via an optical computation is superior to a traditional digital regression.

MOC has been demonstrated to simplify the instrumentation and data analysis requirements of a traditional multivariate calibration. Specifically, the MOE utilizes a thin film interference filter to sense the magnitude of a spectral pattern. A no-moving parts spectrometer highly selective to a particular analyte may be constructed by designing simple calculations based on the filter transmission and reflection spectra. Other research groups have also performed optical computations through the use of weighted integration intervals and acousto-optical tunable filters digital mirror arrays and holographic gratings.

The measurement precision of digital regression has been compared to various optical computing techniques including MOEs, positive/negative interference filters and weighted-integration scanning optical computing. In a high signal condition where the noise of the instrument is limited by photon counting, optical computing offers a higher measurement precision when compared to its digital regression counterpart. The enhancement in measurement precision for scanning instruments is related to the fraction of the total experiment time spent on the most important wavelengths. While the detector integrates or coadds measurements at these important wavelengths, the signal increases linearly while the noise increases as a square root of the signal. Another contribution to this measurement precision enhancement is a combination of the Felgott's and Jacquinot's advantage, which is possessed by MOE optical computing.

While various methodologies have been developed to enhance measurement accuracy in Optical Analysis Systems, the industry requires a system in which the spectral range of the illumination source can be controlled; in which light can be shined directly onto a sample with or without fiber optic probes; and in which the reflected or transmitted light can be analyzed in real time or near real time.

SUMMARY OF THE INVENTION

A method of high-speed processing and monitoring can include moving a plurality of portions of pharmaceutical product past an inspection point, illuminating at least one portion of the pharmaceutical product with a spectral-specific light though an optic window, the window configured to focus the spectral-specific light onto a portion at the inspection point, reflecting light carrying information about the portion through at least one multivariate optical element to produce a first signal, detecting the first signal at a first detector, detecting a deflected portion of the spectral-specific light at a second detector, and determining at high speed at least one selected property of the portion as it moves past the inspection point based upon the detector outputs. The disclosed method also includes measuring and recording the temperature of the system to enable compensation or correction of the detector outputs based on the system temperature.

The portions can comprise pharmaceutical tablets, trays or other containers of powders, or partially- or fully-enclosed sample containers at least partially transparent to light focused onto the portion. The portions can move past the inspection point at a rate between about one portion per second and about five portions per second, with the monitoring occurring in real-time at high speeds.

In another aspect of the invention, a method of high-speed processing and monitoring includes moving a product past an inspection point; illuminating at least a portion of the product with a light; directing light carrying information about the portion through at least one multivariate optical element to produce a first signal; detecting the first signal at a first detector; detecting a deflected portion of the light at a second detector; and determining at high speed at least one selected property of the portion as the portion moves past the inspection point based upon the detector outputs. This aspect of the invention also includes measuring and recording the temperature of the system to enable compensation or correction of the detector outputs based on the system temperature. The product in this aspect may be a pharmaceutical tablet, a pharmaceutical powder, a food product, a chemical, a liquid, a gas, an emulsion, a solution, and/or a mixture.

Additional objects and advantages of the present subject matter are set forth in, or will be apparent to, those of ordinary skill in the art from the detailed description herein. Also, it should be further appreciated that modifications and variations to the specifically illustrated, referred and discussed features and elements hereof may be practiced in various embodiments and uses of the invention without departing from the spirit and scope of the subject matter. Variations may include, but are not limited to, substitution of equivalent means, features, or steps for those illustrated, referenced, or discussed, and the functional, operational, or positional reversal of various parts, features, steps, or the like.

Still further, it is to be understood that different embodiments, as well as different presently preferred embodiments, of the present subject matter may include various combinations or configurations of presently disclosed features, steps, or elements, or their equivalents (including combinations of features, parts, or steps or configurations thereof not expressly shown in the figures or stated in the detailed description of such figures). Additional embodiments of the present subject matter, not necessarily expressed in the summarized section, may include and incorporate various combinations of aspects of features, components, or steps referenced in the summarized objects above, and/or other features, components, or steps as otherwise discussed in this application. Those of ordinary skill in the art will better appreciate the features and aspects of such embodiments, and others, upon review of the remainder of the specification.

BRIEF DESCRIPTION OF THE DRAWINGS

A full and enabling disclosure of the present invention, including the best mode thereof to those of ordinary skill in the art, is set forth more particularly in the remainder of the specification, including reference to the accompanying FIGURE, in which:

FIG. 1 is a top schematic view of an exemplary embodiment of a real time measurement system according to the present invention.

Repeat use of reference characters throughout the present specification and appended drawing is intended to represent same or analogous features or elements of the present subject matter.

DETAILED DESCRIPTION OF THE INVENTION

Detailed reference will now be made to the drawing in which an example embodying the present invention is shown. As used herein, the term "light" is broadly used to mean any form of radiation or radiative energy including, for instance, visible light or light in the infrared region. "Light" is also referred to herein as a light signal, a light beam, a light ray and the like to mean any form of radiative energy in the electromagnetic spectrum. Similarly, the term "transmission" can mean transmission of radiative energy onto a surface of a sample; penetration, however slight, into a sample such as a particulate sample or opaque fluid sample; or passage through a sample.

As used herein, the sample being evaluated can be a solid or a fluid including but not limited to a powder, a pharmaceutical powder mixed with lactose and other excipient materials, a chemical, a polymer, a petroleum product, a solution, a dispersion, an emulsion and combinations of these solids and fluids.

With specific reference now to the drawing, FIG. 1 illustrates the general concept of the present subject matter and is designated generally by reference number 110. As shown in FIG. 1, optical analysis system 110 broadly includes housing 112, illumination or light source 114, chopper wheel 118, one or more spectral elements 120, focusing lens 126, beam splitter 128, a first detector 130 including a multivariate optical element 148, and a second detector 132. Optical analysis system 110 further includes electrical connection 160, pressurization sensor 162, purge gas assembly 164 and temperature sensor 165, which those of ordinary skill in the art will readily understand; therefore, further description is not necessary to understand and practice these aspects of the invention.

With more particular reference to FIG. 1, illumination source 114 provides light 134, which passes through collecting Fresnel lens 116A and into and through spectral element(s) 120. In this example, illumination source 114 is rated for at least about 10,000 hours of operation, which alleviates a need for redundant illumination sources though they may be provided if desired. Also in this example, collecting Fresnel lens 116A is sized to be about 1.5 square inches and is spaced about 0.6 inches from the illumination source 114. Those of ordinary skill in the art will recognize that these dimensions can be adjusted according to particular system requirements and are not meant as limitations of the subject matter but examples only.

As further shown in FIG. 1, light 134 passes through spectral elements 120, which filter out undesired wavelengths to define a desired spectral region, e.g., 1500-2000 nm, in order to target a particular chemical material of interest. Light 134 is focused by focusing Fresnel lens 116B, which may also be sized to be about 1.5 square inches and spaced about 1 inch from chopper wheel 118. As shown, chopper wheel 118 reflects a portion of light 134 as a calibration or reference light 135 and a transmitted light 144. Calibration light 135 is collimated by lens 158 before reflecting from first mirror 124A through adjustable aperture 112B in a bulkhead 112A of the housing 112. Aperture 112B is adjustable to dictate a desired amount of calibration light 135. Finally, calibration light 135 impinges on beam splitter 128 thereby sending portion 135A of calibration light 135 to first MOE detector 130 and portion 135B of calibration light 135 to second or baseline detector 132.

FIG. 1 further illustrates that transmitted light 144 passes from chopper wheel 118 into collimating Fresnel lens 136, which in this example is sized to be about 1.5 square inches and is spaced about 0.6 inches from chopper wheel 118. Transmitted light 144 passes through another adjustable aperture 112C in bulkhead 112A and impinges upon a second mirror 124B, which directs transmitted light 144 toward a sample in container C, such as mixing vat or blender. Those of ordinary skill in the art will recognize that the container could be a conveyor belt or other device for holding or transporting the sample and is not limited to an enclosed container.

As shown in FIG. 1, transmitted light 144 is focused by focusing Fresnel lens 126, which in this example may be round and about 15/16 inches in diameter and is adjustable with an inner tube 122. Also in this example, lens 126 may be positioned about 0.6 inches from an outer surface of the container C. As shown, transmitted light 144, now focused, passes through transmissive window 113, which in this example is approximately 1 inch in diameter and with an anti-reflective (AR) coating disposed on one or both sides of lens 126. The AR coating ensures that the chemical process in the container C does not interfere with the measuring process of optical analysis system 110. Thus, transmitted light 144 enters the container C and reflects from the sample as carrier light 146. The sample can be a moving mixture such as aspirin and an excipient being blended in real time, or a plurality of tablets passing by on a conveyor belt at high speed.

FIG. 1 further illustrates that carrier light 146 is directed by the tube 122 in a direction of the first detector 130. Eventually, carrier light 146 impinges on beam splitter 128 and a portion passes in a direction of detector 132 for baselining with portion 135B of calibration light 135. Another portion of carrier light 146 passes through MOE 148, which as noted above, has been selected for the chemical of interest based on the various components of system 110. Finally, that portion of carrier light 146, having passed through MOE 148, is focused by lens 150 and received by detector 152. As described above, the two signals collected by the detectors 132 and 152 can be manipulated, e.g., mathematically, to extract and ascertain information about the sample carried by the carrier light 146.

In accordance with the present subject matter, temperature sensor 165 can be used to measure and record the temperature of the system shown in FIG. 1. By measuring the system temperature, a known calibration of detector response to system temperature can be applied to the detector outputs. Changes in system temperature are thus compensated for in the system output. In several configurations of the invention, improvements to signal stability can be achieved by accounting for Multivariate Optical Computing systems that have been developed that provide enhanced stability.

There are several factors that can influence the response of a photodetector to a given level of illumination. These factors include a non-linear response to detector responsivity from temperature, the intensity of light, the irradiance, or the shape of the illumination beam. Given the two detectors shown in FIGS. 1, 152 and 156, there are light signals from the calibration path (135A and B) and the sample path (146A and B). By closely matching the amount of light on each detector from each light, system stability improves. Matching the four light levels, in terms of absolute intensity, beam profile (both physical and temporal) provides improved performance. There are several methods to adjust these light beams, including neutral density optical filters, physical apertures, and adjusting reflectivity of appropriate reflective elements. Providing supplemental light on the detectors to change the reference (dark) signal can also be a method of improving the signal stability. All of the system elements can be used in the design of the optical computing system.

Another improvement is provided by controlling the speed of chopper wheel 118, such as using a closed loop control of the speed. It is known that photodetectors may have different responsivities depending on the chopping frequency.

Additional stability is provided by mounting the detectors (152 and 156) rigidly rather than indirectly on the epoxy composite board containing associated amplification circuitry.

The functionality of MOC system 110 and improvements as described above allows for the collection of the entire spectral range of testing simultaneously. This fact is notably different than either a system based on either a scanning lamp or detector system or a discrete diode array detection system. The ability to monitor over the complete spectral range of interest opens up a re-definition of the term "real-time" measurement and analysis. For instance, true real-time process measurements are possible. "Real time" refers to obtaining data without delays attendant to collecting samples or delays due to lengthy computer processing of measurement signals. In the invention described herein, process data can be obtained in an instantaneous or near-instantaneous manner through using the disclosed measurement techniques to directly monitor materials of interest while such materials are undergoing process steps. Long delays due to processing of measurement signals are avoided by optically processing the light as it is reflected from the material(s) of interest.

Although specific examples disclosed herein present monitoring blending of a powdered material and examining solid tablets, the general concept can be extended to other phases. The present system can be utilized in analyzing solids, solutions, emulsions, gases, and dispersions, for example. In addition, while exemplary embodiments discussed herein use reflectance measurements, measurements in a transmission or transflectance mode would also be appropriate.

One of ordinary skill in the art will recognize that differing applications may require modifications and alterations to certain components in order to take full advantage of the presently-disclosed systems. For instance, more diffusion of light has been observed in solid powders relative to liquids; accordingly, different lenses may be needed when a liquid is monitored in order to account for such variations and achieve more accurate measurements.

The presently-disclosed technology can be applied to real-time measurements for a range of industrial applications. These include, but are not limited to monitoring of blending of pharmaceutical powders, including excipients, additives, and active pharmaceutical materials; blending of other powders, including food and chemicals; monitoring dispersions and bi-phasic mixtures (such as insulin, emulsions); and oil and gas applications, including analyzing water content in oil, or oil content in water.

Inclusion of a transmissive window provides physical separation between the measuring device and the process or material being tested. Therefore, this window allows for in-line measurement and/or non-invasive measurement of parameters such as chemical functionality, including alcohol content of petroleum fractions or tackifier resins. Environmental applications are also conceivable, such as stack gas analysis, including measurement of NOx, SOx, CO, CO2, or other gases in a gas stream; wastewater analysis and treatment monitoring; and hazardous substance monitoring applications such as mercury vapor detection.

As noted above, MOC technology can be used to monitor a wide variety of materials as the materials are subjected to different processes. For instance, the mixing of powders can be monitored. As materials are blended, the existing art does not allow for continuous, real-time, in-line measurement. Current limitations are the result of several factors including: moving of the powders being measured during the course of data acquisition and the need to connect analytical equipment to the measurement point using fiber optic cables. This optical analysis system is designed to allow for instantaneous measurement using a measurement point located on the vessel.

Other embodiments of the present subject matter include real time measurement of flowing materials. In such embodiments, the sampling window(s) may be located on a pipe or vessel such that interrogating illumination can be applied to the material. For instance, a port could be included on a pipe to allow for sampling of the material inside the pipe. The window may be positioned directly on the pipe, or on a small diversion away from the main flow path, as appropriate under the circumstances. Such embodiments could also include sampling of vapor systems within a stack to monitor combustion gases or flowing process stream such as water containing other materials.

Still further embodiments of the present invention include the real time measurement of materials in containers, such as vials or bins where the container is either at least partially open to the outside environment or transmissive to the sampling illumination. Such containers could be stationary or in motion. A container could also include a conveyor or trough carrying material. Typical applications could include the monitoring the progress of a chemical reaction or the content of samples moving past a measurement location.

The present subject matter may be better understood from the following tests and examples.

In Example I/System I, a first breadboard system was constructed and used to test a mixture of powders using the following components:
  Illumination: 20 W Gilway lamp
  Spectral elements: 5 mm deuterium oxide ($D_2O$), 5 mm Germanium
  Optical window: fiber optic probe
  Detector: InAr detector from Judson
  MOE: specific to test The procedure and results of static testing using System I were as follows: A powdered sample with a known composition was placed in a dish and the fiber optic probe was placed in contact with the powder. The output of the detectors was monitored and recorded.

In Example II/System II, a system similar to the optical analysis system 10 shown in the figures was constructed and used to make static measurements on aspirin/lactose using the following components:

Illumination: 20 W Gilway lamp
Spectral elements: 5 mm $D_2O$, 5 mm Germanium
Optical window: none
Detector: PbS detector from New England Photoconductor
MOE: specific to test conditions.

The procedure and results of static testing using System II were as follows: A powdered sample with a known composition was placed in a dish and the system light beam was focused on the powder. The output of the detectors was monitored and recorded. Aspirin/lactose samples covering the range of 100% aspirin to 100% lactose were tested.

In Example III/System III, a system similar to the optical analysis system 10 shown in the figures was constructed and used to make dynamic measurements on aspirin/lactose using the following components:

Illumination: 20 W Gilway lamp
Spectral elements: 5 mm $D_2O$, 5 mm Germanium
Optical window: sapphire window
Detector: PbS detector from New England Photoconductor
MOE: specific to test conditions.

The procedure and results of dynamic testing using System III were as follows: The Aspirin/Lactose testing was made on a mixer bowl containing lactose and the system measured as aspirin was added to the system and mixed. Specifically, lactose powder was placed in the bowl of a mixer and the measurement system was attached the bowl using a Swagelok® brand fitting. A sapphire window was used to contain the powder in the bowl and allow the system to interrogate the powder. With the mixer turning, known amounts of aspirin were added and the system output signal was monitored and recorded. Aspirin was added in several allotments to about 37% final aspirin concentration.

In Example IV/System IV, a system similar to the optical analysis system 10 shown in the figures was constructed and used to make static measurements on aspirin/lactose using the following components:

Illumination: 5 W Gilway lamp
Spectral elements: 5 mm $D_2O$, 5 mm Germanium
Optical window: none
Detector: PbS detector from New England Photoconductor
MOE: specific to test conditions.

The procedure and results of dynamic testing using System III were similar to the examples above.

Although the invention has been described in such a way as to provide an enabling disclosure for one of ordinary skill in the art to make and use the invention, it should be understood that the descriptive examples of the invention are not intended to limit the present invention to use only as shown in the figures. For instance, the housing can be shaped as a square, an oval, or in a variety of other shapes.

Further, a variety of light sources can be substituted for those described above. It is intended to claim all such changes and modifications as fall within the scope of the appended claims and their equivalents. Thus, while exemplary embodiments of the invention have been shown and described, those of ordinary skill in the art will recognize that changes and modifications may be made to the foregoing examples without departing from the scope and spirit of the invention.

What is claimed is:

1. A method for high-speed analysis of samples, comprising:
    illuminating at least a portion of a sample with light at an inspection point;
    providing an analysis system comprising a light sensitive detector, the detector producing an output based on received light;
    measuring and recording a temperature of the system including the detector;
    directing light from the sample portion toward the light sensitive detector through at least one multivariate optical element, the light from the sample portion carrying information about the sample portion;
    directing at least a portion of the sample illuminating light toward the light sensitive detector through a reference optical element; and
    analyzing signals detected by the detector, the analysis being based on a comparison of a signal produced from light passing through the at least one multivariate optical element and a signal produced from light passing through the reference optical element,
    wherein the detector output resulting from the signals is compensated or corrected based on the system temperature.

2. The method of claim 1, wherein the sample is at least one of a pharmaceutical tablet, a pharmaceutical powder, a food material, a chemical, a liquid, a gas, an emulsion, a solution, or a mixture thereof.

3. The method of claim 1, wherein the sample is a powder mixture in a closed container, the container being at least partially transparent to the illuminating light.

4. The method of claim 1, further comprising: moving the sample past the inspection point.

5. The method of claim 1, wherein directing light from the sample portion comprises directing light reflected from the sample portion.

6. The method of claim 1, wherein directing light from the sample portion comprises directing light transmitted through the sample portion.

7. The method of claim 1, wherein illuminating comprises illuminating the sample with a spectral-specific light.

8. The method of claim 7, further comprising: illuminating the sample through an optic window, the optic window being configured to focus the spectral-specific light onto a sample portion at the inspection point.

9. The method of claim 1, wherein the sample comprises a plurality of discrete portions.

10. The method of claim 9, wherein the plurality of discrete portions are disposed in closed containers, the containers at least partially transparent to the spectral-specific light.

11. A method for high-speed analysis of samples using an analysis system, comprising:
    illuminating at least a portion of a sample with light at an inspection point;
    providing a light sensitive detector, the detector producing an output based on received light;
    measuring and recording a temperature of the system;
    directing light from the sample portion toward the light sensitive detector through at least one multivariate optical element, the light from the sample portion carrying information about the sample portion;
    directing at least a portion of the sample illuminating light toward the light sensitive detector through a reference optical element; and
    analyzing signals produced by the detector, the analysis being based on a comparison of the signal produced from light passing through the at least one multivariate optical element and the signal produced from light passing through the reference optical element,
    wherein the detector outputs are corrected based on the system temperature, wherein directing light toward the light sensitive detector comprises directing light through a plurality of multivariate optical elements, and wherein directing a portion of the sample illuminating light comprises directing a portion of the sample illuminating light through a plurality of reference optical elements.

12. The method of claim 11, wherein directing light comprises directing light alternately through differing multivariate optical elements and corresponding reference elements in sequence.

13. The method of claim 1, wherein providing a light sensitive detector comprises: providing a first light sensitive detector and a second light sensitive detector, wherein the first light sensitive detector receives light carrying information about the sample portion, wherein the second light sensitive detector receives light passing through the reference optical element, and wherein signals from both the first and second light sensitive detectors are compensated or corrected based on the system temperature.

14. The method of claim 1, wherein the sample is a hydrocarbon mixture of oil and gas.

15. The method of claim 14, wherein the oil and gas mixture is flowing material in an oil and gas wellbore.

16. The method of claim 1, wherein the inspection point is in an oil and gas wellbore.

17. The method of claim 16, wherein the inspection point is in a vessel inserted into an oil and gas wellbore.

18. A method for high-speed analysis of samples in an oil and gas application, comprising:

deploying a vessel having an inspection point into a flowing sample stream within an oil and gas wellbore;

illuminating at least a portion of a sample with light at an inspection point;

providing a light sensitive detector, the detector producing an output based on received light;

measuring and recording a temperature of the system, including the detector;

directing light from the sample portion toward the light sensitive detector through at least one multivariate optical element, the light from the sample portion carrying information about the sample portion;

directing at least a portion of the sample illuminating light toward the light sensitive detector through a reference optical element; and analyzing signals detected by the detector, the analysis being based on a comparison of a signal produced from light passing through the at least one multivariate optical element and a signal produced from light passing through the reference optical element, wherein the detector output resulting from the signals is corrected based on the measured system temperature.

* * * * *